US009955983B2

(12) United States Patent
Aghazadeh

(10) Patent No.: US 9,955,983 B2
(45) Date of Patent: May 1, 2018

(54) SYSTEMS AND METHODS FOR PROVIDING ALIGNMENT IN TOTAL KNEE ARTHROPLASTY

(71) Applicant: ARTHROMEDA, INC., Lowell, MA (US)

(72) Inventor: Mehran S. Aghazadeh, Newton, MA (US)

(73) Assignee: ARTHROMEDA, INC., Lowell, MA (US)

( * ) Notice: Subject to any disclaimer, the term of this patent is extended or adjusted under 35 U.S.C. 154(b) by 0 days. days.

(21) Appl. No.: 15/465,551

(22) Filed: Mar. 21, 2017

(65) Prior Publication Data

US 2017/0252050 A1    Sep. 7, 2017

Related U.S. Application Data

(63) Continuation of application No. 14/215,886, filed on Mar. 17, 2014, now Pat. No. 9,597,096.

(60) Provisional application No. 61/789,421, filed on Mar. 15, 2013.

(51) Int. Cl.
*A61B 17/17* (2006.01)
*A61B 17/15* (2006.01)
*A61F 2/46* (2006.01)

(52) U.S. Cl.
CPC ........ *A61B 17/1764* (2013.01); *A61B 17/155* (2013.01); *A61B 17/157* (2013.01); *A61F 2/4657* (2013.01); *A61F 2002/4632* (2013.01); *A61F 2002/4633* (2013.01); *A61F 2002/4668* (2013.01)

(58) Field of Classification Search
CPC ............................ A61F 2/461; A61B 17/1764
See application file for complete search history.

(56) References Cited

U.S. PATENT DOCUMENTS

| 5,007,936 A | 4/1991 | Woolson |
| 5,527,317 A | 6/1996 | Ashby et al. |
| 5,652,926 A | 7/1997 | Saito |
| 5,658,294 A | 8/1997 | Sederholm |
| 5,700,268 A | 12/1997 | Bertin |

(Continued)

FOREIGN PATENT DOCUMENTS

| WO | 2012/064513 A1 | 5/2012 |
| WO | 2012/113054 A1 | 8/2012 |

OTHER PUBLICATIONS

Drstvensek, I., et al., "Patient Specific Instruments for Total Hip Replacement Surgery," Academic Journal of Manufacturing Engineering, 2013, v. 11, pp. 6-9.

(Continued)

*Primary Examiner* — Christopher Beccia
(74) *Attorney, Agent, or Firm* — Nutter McClennen & Fish LLP

(57) ABSTRACT

Systems and methods for providing alignment in total knee arthroplasty operations are provided herein. The systems and methods generally include a plurality of sensors coupled to a patient's bones or other surgical tools, the sensors detect their position and orientation in space and communicate this information to a processor. The processor can utilize the information to display data to a surgeon or other user regarding the position, angle, and alignment of a patient's bones, surgical tools, and the reconstructed knee joint.

7 Claims, 16 Drawing Sheets

(56) References Cited

U.S. PATENT DOCUMENTS

| | | | |
|---|---|---|---|
| 5,737,645 A | 4/1998 | Saito | |
| 5,768,134 A | 6/1998 | Swaelens et al. | |
| 5,879,402 A | 3/1999 | Lawes et al. | |
| 6,027,507 A | 2/2000 | Anderson et al. | |
| 6,126,608 A | 10/2000 | Kemme et al. | |
| 6,128,445 A | 10/2000 | Nakamura | |
| 6,162,191 A | 12/2000 | Foxlin | |
| 6,214,014 B1 | 4/2001 | McGann | |
| 6,245,109 B1 | 6/2001 | Mendes et al. | |
| 6,383,149 B1 | 5/2002 | DeMayo | |
| 6,573,706 B2 | 6/2003 | Mendes et al. | |
| 6,583,630 B2 | 6/2003 | Mendes et al. | |
| 6,685,655 B2 | 2/2004 | DeMayo | |
| 6,781,705 B2 | 8/2004 | Waslowski et al. | |
| 6,827,723 B2 * | 12/2004 | Carson | A61B 34/20 606/130 |
| 6,847,435 B2 | 1/2005 | Honda et al. | |
| 6,855,118 B2 | 2/2005 | Linton | |
| 6,917,827 B2 | 7/2005 | Kienzle, III | |
| 6,931,746 B2 | 8/2005 | Pourmanafzadeh | |
| 7,022,141 B2 | 4/2006 | Dwyer et al. | |
| 7,074,224 B2 | 7/2006 | Daniels et al. | |
| 7,372,771 B2 | 5/2008 | Park | |
| 7,382,443 B2 | 6/2008 | Ohtomo et al. | |
| 7,559,931 B2 | 7/2009 | Stone | |
| 7,679,728 B2 | 3/2010 | Kurokawa | |
| 7,780,672 B2 | 8/2010 | Metzger et al. | |
| 7,854,737 B2 | 12/2010 | Daniels et al. | |
| 7,877,131 B2 | 1/2011 | Jansen et al. | |
| 7,967,868 B2 | 6/2011 | White et al. | |
| 7,981,158 B2 | 7/2011 | Fitz et al. | |
| 8,048,167 B2 | 11/2011 | Dietz et al. | |
| 8,057,479 B2 | 11/2011 | Stone | |
| 8,057,482 B2 | 11/2011 | Stone et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,083,745 B2 | 12/2011 | Lang et al. | |
| 8,088,169 B2 | 1/2012 | Dorr et al. | |
| 8,092,465 B2 | 1/2012 | Metzger et al. | |
| 8,105,330 B2 | 1/2012 | Fitz et al. | |
| 8,118,815 B2 | 2/2012 | van der Walt | |
| 8,133,234 B2 | 3/2012 | Meridew et al. | |
| 8,175,683 B2 | 5/2012 | Roose | |
| 8,221,430 B2 | 7/2012 | Park et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld et al. | |
| 8,337,501 B2 | 12/2012 | Fitz et al. | |
| 8,361,163 B2 | 1/2013 | Quaid | |
| 8,377,066 B2 | 2/2013 | Katrana et al. | |
| 8,390,792 B2 | 3/2013 | Rung et al. | |
| 8,398,646 B2 | 3/2013 | Metzger et al. | |
| 8,407,067 B2 | 3/2013 | Uthgenannt et al. | |
| 8,414,591 B2 | 4/2013 | De Smedt et al. | |
| 8,439,978 B2 | 5/2013 | Ebbitt | |
| 8,463,577 B2 | 6/2013 | Yuen et al. | |
| 8,473,305 B2 | 6/2013 | Belcher et al. | |
| 8,480,679 B2 | 7/2013 | Park et al. | |
| 8,486,150 B2 | 7/2013 | White et al. | |
| 8,500,740 B2 | 8/2013 | Bojarski et al. | |
| 8,514,125 B2 | 8/2013 | Van Zeijl et al. | |
| 8,514,376 B2 | 8/2013 | D'Aligny et al. | |
| 8,529,578 B2 | 9/2013 | Daniels et al. | |
| 8,535,387 B2 | 9/2013 | Meridew et al. | |
| 8,545,509 B2 | 10/2013 | Park et al. | |
| 8,551,099 B2 | 10/2013 | Lang et al. | |
| 8,551,169 B2 | 10/2013 | Fitz et al. | |
| 8,568,487 B2 | 10/2013 | Witt et al. | |
| 8,585,708 B2 | 11/2013 | Fitz et al. | |
| 8,588,892 B2 | 11/2013 | Hladio et al. | |
| 8,591,516 B2 | 11/2013 | Metzger et al. | |
| 8,597,298 B2 | 12/2013 | Daniels et al. | |
| 8,603,180 B2 | 12/2013 | White et al. | |
| 8,608,748 B2 | 12/2013 | Metzger et al. | |
| 8,608,749 B2 | 12/2013 | Meridew et al. | |
| 8,611,504 B2 | 12/2013 | Kubiak et al. | |
| 8,617,171 B2 | 12/2013 | Park et al. | |
| 8,623,026 B2 | 1/2014 | Wong et al. | |
| 8,632,547 B2 | 1/2014 | Maxson et al. | |
| 8,657,827 B2 | 2/2014 | Fitz et al. | |
| 8,696,758 B2 | 4/2014 | Hood et al. | |
| 8,702,807 B2 | 4/2014 | Hood et al. | |
| 8,705,953 B2 | 4/2014 | Schriefer | |
| 8,715,289 B2 | 5/2014 | Smith | |
| 8,715,291 B2 | 5/2014 | Park et al. | |
| 8,737,700 B2 | 5/2014 | Park et al. | |
| 8,777,875 B2 | 7/2014 | Park | |
| 8,790,346 B2 | 7/2014 | Daniels et al. | |
| 8,801,719 B2 | 8/2014 | Park et al. | |
| 8,801,720 B2 | 8/2014 | Park et al. | |
| 8,828,087 B2 | 9/2014 | Stone et al. | |
| 8,852,188 B2 | 10/2014 | Daniels et al. | |
| 8,852,189 B2 | 10/2014 | Daniels et al. | |
| 8,852,198 B2 | 10/2014 | De Smedt et al. | |
| 8,858,561 B2 | 10/2014 | White et al. | |
| 8,861,818 B2 | 10/2014 | Ito et al. | |
| 8,864,769 B2 | 10/2014 | Stone et al. | |
| 8,868,377 B2 | 10/2014 | Yuen et al. | |
| 8,882,779 B2 | 11/2014 | Park et al. | |
| 8,888,786 B2 | 11/2014 | Stone et al. | |
| 8,900,244 B2 | 12/2014 | Meridew et al. | |
| 8,900,246 B2 | 12/2014 | Lashure et al. | |
| 8,911,447 B2 | 12/2014 | van der Walt et al. | |
| 8,932,299 B2 | 1/2015 | Bono et al. | |
| 8,939,982 B2 | 1/2015 | Chellaoui | |
| 8,951,259 B2 | 2/2015 | Fitz et al. | |
| 8,961,527 B2 | 2/2015 | Park | |
| 8,968,320 B2 | 3/2015 | Park et al. | |
| 8,974,467 B2 | 3/2015 | Stone | |
| 8,974,468 B2 | 3/2015 | Borja | |
| 8,979,856 B2 | 3/2015 | Catanzarite et al. | |
| 8,979,936 B2 | 3/2015 | White et al. | |
| 8,984,731 B2 | 3/2015 | Broeck et al. | |
| 8,986,309 B1 | 3/2015 | Murphy | |
| 8,998,909 B2 | 4/2015 | Gillman et al. | |
| 8,998,910 B2 | 4/2015 | Borja et al. | |
| 9,005,297 B2 | 4/2015 | Katrana et al. | |
| 9,011,456 B2 | 4/2015 | Ranawat et al. | |
| 9,017,337 B2 | 4/2015 | Bartelme et al. | |
| 9,020,788 B2 | 4/2015 | Lang et al. | |
| 9,023,050 B2 | 5/2015 | Lang et al. | |
| 9,072,531 B2 | 7/2015 | Fitz et al. | |
| 9,084,617 B2 | 7/2015 | Lang et al. | |
| 9,107,679 B2 | 8/2015 | Lang et al. | |
| 9,107,680 B2 | 8/2015 | Fitz et al. | |
| 9,113,823 B2 | 8/2015 | Yuen et al. | |
| 9,113,921 B2 | 8/2015 | Lang et al. | |
| 9,113,971 B2 | 8/2015 | Metzger et al. | |
| 9,121,702 B2 | 9/2015 | Kimura | |
| 9,138,258 B2 | 9/2015 | Geebelen | |
| 9,138,319 B2 | 9/2015 | Fanson et al. | |
| 9,168,103 B2 | 10/2015 | Hladio et al. | |
| 9,168,153 B2 | 10/2015 | Bettenga | |
| 9,173,661 B2 | 11/2015 | Metzger et al. | |
| 9,186,161 B2 | 11/2015 | Lang et al. | |
| 9,192,392 B2 | 11/2015 | van der Walt et al. | |
| 9,198,760 B2 | 12/2015 | Geebelen | |
| 9,204,977 B2 | 12/2015 | Bollinger | |
| 9,211,128 B2 | 12/2015 | Gillman et al. | |
| 9,241,745 B2 | 1/2016 | Smith et al. | |
| 9,265,509 B2 | 2/2016 | Park et al. | |
| 9,271,744 B2 | 3/2016 | Meridew | |
| 9,289,253 B2 | 3/2016 | Vanasse et al. | |
| 9,408,617 B2 | 8/2016 | Ranawat et al. | |
| 9,597,096 B2 | 3/2017 | Aghazadeh | |
| 2002/0077540 A1 | 6/2002 | Kienzle | |
| 2005/0113846 A1 | 5/2005 | Carson | |
| 2005/0148855 A1 | 7/2005 | Kienzle | |
| 2006/0190011 A1 | 8/2006 | Ries | |
| 2006/0264731 A1 | 11/2006 | Murphy | |
| 2007/0186738 A1 * | 8/2007 | McGinley | A61B 17/157 83/88 |
| 2008/0021479 A1 | 1/2008 | Penenberg | |

(56) References Cited

U.S. PATENT DOCUMENTS

| | | |
|---|---|---|
| 2008/0257363 A1 | 10/2008 | Schoenefeld et al. |
| 2009/0099570 A1 | 4/2009 | Paradis et al. |
| 2009/0151736 A1 | 6/2009 | Belcher et al. |
| 2009/0204222 A1 | 8/2009 | Burstein et al. |
| 2009/0318836 A1 | 12/2009 | Stone et al. |
| 2009/0318930 A1 | 12/2009 | Stone et al. |
| 2010/0063509 A1 | 3/2010 | Borja et al. |
| 2010/0064216 A1* | 3/2010 | Borja .................. A61B 17/157 715/705 |
| 2010/0076505 A1 | 3/2010 | Borja |
| 2010/0100011 A1 | 4/2010 | Roche |
| 2010/0137871 A1 | 6/2010 | Borja |
| 2010/0217270 A1 | 8/2010 | Polinski et al. |
| 2010/0274253 A1 | 10/2010 | Ure |
| 2010/0312350 A1 | 12/2010 | Bonutti |
| 2011/0046735 A1 | 2/2011 | Metzger et al. |
| 2011/0092804 A1 | 4/2011 | Schoenefeld et al. |
| 2011/0160736 A1 | 6/2011 | Meridew et al. |
| 2011/0172672 A1 | 7/2011 | Dubeau et al. |
| 2011/0190775 A1 | 8/2011 | Ure |
| 2011/0190899 A1 | 8/2011 | Pierce et al. |
| 2011/0208093 A1 | 8/2011 | Gross et al. |
| 2012/0123423 A1 | 5/2012 | Fryman |
| 2012/0226283 A1 | 9/2012 | Meridew et al. |
| 2012/0245647 A1 | 9/2012 | Kunz et al. |
| 2012/0289965 A1 | 11/2012 | Gelaude et al. |
| 2012/0303004 A1 | 11/2012 | Uthgenannt et al. |
| 2012/0316567 A1 | 12/2012 | Gross et al. |
| 2013/0158671 A1 | 6/2013 | Uthgenannt et al. |
| 2013/0190887 A1 | 7/2013 | Fanson et al. |
| 2013/0197529 A1 | 8/2013 | Metzger et al. |
| 2013/0274633 A1 | 10/2013 | Hladio et al. |
| 2014/0005531 A1 | 1/2014 | Taylor |
| 2014/0018934 A1 | 1/2014 | Meridew et al. |
| 2014/0052149 A1 | 2/2014 | van der Walt et al. |
| 2014/0052270 A1 | 2/2014 | Witt et al. |
| 2014/0074441 A1 | 3/2014 | Fitz et al. |
| 2014/0081275 A1 | 3/2014 | Metzger et al. |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0135658 A1 | 5/2014 | Hladio et al. |
| 2014/0135775 A1 | 5/2014 | Maxson et al. |
| 2014/0135940 A1 | 5/2014 | Goldstein et al. |
| 2014/0275940 A1 | 9/2014 | Hladio et al. |
| 2014/0276864 A1 | 9/2014 | Aghazadeh |
| 2014/0276867 A1 | 9/2014 | Kelley et al. |
| 2014/0276870 A1 | 9/2014 | Eash |
| 2014/0276871 A1 | 9/2014 | Sherman et al. |
| 2014/0276872 A1 | 9/2014 | Song |
| 2014/0324058 A1 | 10/2014 | Metzger et al. |
| 2014/0330281 A1 | 11/2014 | Aghazadeh |
| 2014/0336661 A1 | 11/2014 | Stuchin |
| 2014/0364858 A1 | 12/2014 | Li et al. |
| 2014/0378979 A1 | 12/2014 | Stone et al. |
| 2015/0105784 A1 | 4/2015 | Bono et al. |
| 2015/0112348 A1 | 4/2015 | Schoenefeld et al. |
| 2015/0127009 A1 | 5/2015 | Berend et al. |
| 2015/0133945 A1 | 5/2015 | Dushyant et al. |
| 2015/0150569 A1 | 6/2015 | van der Walt et al. |
| 2015/0164657 A1 | 6/2015 | Miles et al. |
| 2015/0182292 A1 | 7/2015 | Hladio et al. |
| 2015/0238204 A1 | 8/2015 | Stone |
| 2015/0238272 A1 | 8/2015 | Ranawat et al. |
| 2015/0272478 A1 | 10/2015 | Borja |
| 2015/0272696 A1 | 10/2015 | Fry et al. |
| 2015/0313684 A1 | 11/2015 | Fanson et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2015/0351778 A1 | 12/2015 | Uthgenannt et al. |
| 2016/0008013 A1 | 1/2016 | Metzger et al. |
| 2016/0015466 A1 | 1/2016 | Park et al. |
| 2016/0038160 A1 | 2/2016 | Metzger et al. |
| 2016/0038161 A1 | 2/2016 | Gibson |
| 2016/0038242 A1 | 2/2016 | Lo Iacono et al. |
| 2016/0038307 A1 | 2/2016 | Bettenga |
| 2016/0058577 A1 | 3/2016 | Gillman et al. |
| 2016/0100845 A1 | 4/2016 | Smith et al. |
| 2016/0128706 A1 | 5/2016 | Meridew |
| 2016/0135824 A1 | 5/2016 | Vanasse et al. |

OTHER PUBLICATIONS

Extended European Search Report for Application No. 14763891.0, dated Sep. 15, 2016 (6 pages).

International Search Report and Written Opinion for Application No. PCT/US2014/030331, dated Aug. 29, 2014 (22 pages).

* cited by examiner

SYSTEMS AND METHODS FOR PROVIDING ALIGNMENT IN TOTAL KNEE ARTHROPLASTY

CROSS-REFERENCE TO RELATED APPLICATIONS

This application is a continuation of U.S. application Ser. No. 14/215,886, filed Mar. 17, 2014, now issued as U.S. Pat. No. 9,597,096, entitled "Systems and Methods for Providing Alignment in Total Knee Arthroplasty," which claims the benefit of U.S. Provisional Application No. 61/789,421, filed Mar. 15, 2013, entitled "Systems and Methods for Providing Alignment in Total Knee Arthroplasty." Each of these applications are incorporated by reference in their entirety.

FIELD OF THE INVENTION

The present invention relates to surgical procedures and, in particular, to systems and methods for aligning anatomical structures and surgical components during total knee arthroplasty operations.

BACKGROUND

Total Knee Arthroplasty

The knee is the largest joint in the human body. As shown in FIGS. 1 and 7A, the knee 100 includes the lower end of the femur 102 (thigh bone), the upper end of the tibia 104 (shin bone), and the inner surface of the patella 106 (knee cap, see FIG. 7A). The femur rotates over the tibia and the patella glides in a groove on the end of the femur in front (i.e., anterior). The inner surface of these bony components is covered by cartilage 106 that, along with joint fluid, provides smooth motion of the joint and shock absorption. Various ligaments and muscles help in keeping the knee strong and stable.

Arthritis is a condition where the cartilage 106 starts wearing away and the knee becomes stiff and painful. FIGS. 2 and 3A illustrate a knee exhibiting osteoarthritis, including deterioration of the cartilage 106. As the condition worsens, bone can rub against bone, causing even more pain and loss of function. Knee replacement surgery, also known as knee arthroplasty, is the indicated treatment for many arthritic joint conditions and involves replacing the painful joint with an artificial prosthesis. During knee replacement surgery, the proximal end of the tibia and the distal end of the femur are exposed by an incision made in front (i.e., anterior) of the knee. These bony structures are then cut and shaped to accept prosthetic implants, as shown in FIG. 3B. FIG. 4 illustrates alternative views of knee arthroplasty prosthesis, including a polyethylene implant 402 that is often placed on an inner surface of the patella during the procedure.

FIG. 5 illustrates one embodiment of a total knee prosthesis 500 in isolation. The prosthesis 500 typically includes four components:
1. Femoral component 502, made of a metal material and designed to replace the articular surface and subchondral bone of the distal end of the femur 102;
2. Tibial component 504, made of a metal material and designed to replace the subchondral bone of the proximal tibia 104. This component can also be formed from alternative materials, such as polyethylene;
3. Insert 506, typically formed from polyethylene and designed to provide a bearing surface between the femoral and tibial components 502, 504. It is typically fixed over the tibial component 504 by a locking mechanism; and
4. Patella component 402, made from polyethylene as described above and designed to replace the articular surface of the patella.

Total Knee Arthroplasty (TKA), when successful, can result in rapid improvement in pain, joint function, and quality of life for a majority of patients.

The frequent success of the procedure, in combination with an aging population, has caused demand for TKA procedures to increase rapidly. In 2003 alone, 402,100 TKA operations were performed. With a continued rapid increase in demand, there are projected be close to 3.5 million TKA operations in 2030. The increasing demand for this procedure will put a burden on the health care system in at least two ways: (1) by stressing the number of well trained surgeons and (2) by increasing overall expense.

One strategy to help meet this demand is to reduce the required operation time and improve the outcome of TKA procedures. Spending less time during a primary TKA, and eliminating the need for any subsequent revision procedure, will save time and allow for a higher volume of these procedures to be performed.

Recurrent Surgical Problems

Arthritic knee joints usually present with different degrees of deformity and misalignment because of various degradations and changes in cartilaginous and bony components of the joint. Compared to the normal knee anatomy 602 shown in FIG. 6, there are typically two different types of misalignment: (1) varus deformity 604 (i.e., bow legged) and (2) valgus deformity 606 (i.e., knock knees). One important goal of a TKA procedure is to restore optimal biomechanical alignment in a reconstructed joint. This is because a properly aligned joint will have better function, result in higher patient satisfaction, and increase the longevity of the reconstructed joint.

Proper alignment can be achieved by making different cuts in the distal femur and proximal tibia in relation with various planes and axes of these long bones. As shown in FIGS. 7A-7C and 8 illustrate a typical progression of a TKA operation, in which various cuts are made in the femur and tibia to prepare the bones to receive prostheses. To make the cuts, any of a variety of cutting guides (also known as cutting blocks or jigs) are typically placed next to the bones after they are exposed. The cutting guides provide a reference plane for cutting the bone using a special saw. As can be expected, the cutting blocks have to be precisely positioned at proper angles relative to the bone to ensure correct placement of the prostheses and subsequent alignment of the reconstructed joint. Accordingly, any of a variety of alignment devices can be employed to position the cutting guides, including, for example, the femoral intramedullary alignment device 900 shown in FIG. 9 and the tibial extramedullary alignment device 1000 shown in FIG. 10.

Unfortunately, most alignment devices available today and designed for this purpose are either not precise enough, very expensive, or both. Indeed, the bone cuts, and consequently the reconstructed joint alignment, is often not as it was intended to be when using these devices.

Currently Available Options

There are three classes of alignment devices currently available:
1. Mechanical instruments, including intramedullary or extra-medullary devices like those shown in FIGS. 9 and 10;

2. Computerized navigation systems, which utilize specialized computers, stereoscopic cameras, and marker structures to track the three-dimensional positioning of objects attached to the marker structures; and
3. Custom-made cutting blocks that align with the shape of a specific patient's bones in a manner that results in correctly oriented bone cuts.

More recently, another option has been introduced that involves creating a custom set of prostheses for each particular patient's anatomy. All of these options, however, suffer from the problems mentioned above—that is, they are extremely expensive, too imprecise, or both. In addition, the patient-specific devices and prostheses can require additional time and visitation with a surgeon to image the patient's anatomy, design the custom components, and fabricate them in advance of a TKA procedure.

SUMMARY

The systems and methods described herein address the problems discussed above by providing more accurate and more precise alignment of anatomical structures, prostheses, and surgical tools during total knee arthroplasty (TKA) operations. In general, the systems and methods described herein employ a plurality of sensor units capable of detecting their position and orientation in space and communicating that information to a digital data processor. By attaching the sensors to any of a patient's bone, a calibration instrument, a cutting guide, or other surgical tools, software executing on the digital data processor can determine the three-dimensional position of, for example, the patient's bones (e.g., the femur and tibia), the cutting guides, or other tools/instruments. The positions of one or more of these components can be updated continuously throughout the operation, and can aid surgeons in more efficiently and more accurately completing a TKA procedure. The systems and methods described herein have a number of advantages over the prior art, including increased accuracy and precision, as well as reduced cost due to simple configuration and the use of readily-available components. In addition, the systems and methods described herein can be easily reused with multiple patients without requiring the fabrication of custom components.

In one aspect, a system for optimizing the alignment of a bone cutting guide for placement of a total knee prosthesis component is provided that includes a first bone sensor that can be adapted to be fixed to a first bone and has a sensor for determining the orientation of the first bone sensor and a transmitter for transmitting orientation data wirelessly. The system can further include a first bone guide having a plurality of probes configured to contact anatomical features of the first bone to establish a known geometry with respect to a mechanical axis of the first bone. The first bone guide can include a first bone guide sensor having a sensor determining the orientation of the first bone guide and a transmitter for transmitting orientation data wirelessly. The system can also include a first bone cutting guide having one or more features for attaching to the patient's anatomy proximate to the first bone. The first bone cutting guide can include a first bone cutting guide sensor having a sensor determining the orientation of the first bone cutting guide and a transmitter for transmitting orientation data wirelessly. The system can further include a processing unit comprising a computer processor coupled to a non-transitory memory and a display. The memory can store software instructions causing the computer processor to: (i) receive orientation data wirelessly from the first bone sensor, (ii) receive orientation data wirelessly from the first bone guide sensor, (iii) apply the orientation data from the first bone guide sensor and the first bone sensor to calculate angular offsets that calibrate the first bone sensor's orientation data to reflect the orientation of the mechanical axis of the first bone, (iv) receive orientation data wirelessly from the first bone cutting guide sensor, and (v) display to a user a difference between the orientation of the mechanical axis of the first bone and the orientation of the first bone cutting guide.

The systems and methods described herein can include any of a variety of additional or alternative features and/or components, all of which are considered within the scope of the present invention. For example, the systems and methods described herein can be applied to a number of different anatomical structures in the body. In some embodiments, for example, the first bone can be a tibia. In such embodiments, the first bone guide can include at least one tubercle probe and at least one malleolus probe. In other embodiments, the first bone guide can further include a spine probe and at least two malleolus probes. In still other embodiments, the first bone cutting guide can be arranged to guide a cut that is oriented at a 90 degree angle to the mechanical axis of the first bone, though, in other embodiments, different orientation angles can be utilized.

In certain embodiments, the first bone can be a femur rather than a tibia. In such embodiments, the first bone guide can be configured to contact the femoral shaft. In addition, the first bone guide can include two parallel and equal height probes for contacting the femoral shaft.

In some embodiments, the system can further include a second bone sensor that can be adapted to be fixed to a second bone and can have a sensor for determining the orientation of the second bone sensor and a transmitter for transmitting orientation data wirelessly. The system can also include a second bone guide having a plurality of probes configured to contact anatomical features of the second bone to establish a known geometry with respect to a mechanical axis of the second bone. The second bone guide can include a second bone guide sensor having a sensor determining the orientation of the second bone guide and a transmitter for transmitting orientation data wirelessly. The system can further include a second bone cutting guide having one or more features for attaching to the patient's anatomy proximate to the second bone, and the second bone cutting guide can include a second bone cutting guide sensor having a sensor determining the orientation of the second bone cutting guide and a transmitter for transmitting orientation data wirelessly. Furthermore, the non-transitory memory of the processing unit can further include software instructions causing the computer processor to: (i) receive orientation data wirelessly from the second bone sensor, (ii) receive orientation data wirelessly from the second bone guide sensor, (iii) apply the orientation data from the second bone guide sensor and the second bone sensor to calculate angular offsets that calibrate the second bone sensor's orientation data to reflect the orientation of the mechanical axis of the second bone, (iv) receive orientation data wirelessly from the second bone cutting guide sensor, and (v) display to a user a difference between the orientation of the mechanical axis of the second bone and the orientation of the second bone cutting guide.

As noted above, in certain embodiments the first bone can be a tibia and the second bone can be a femur. In this manner, the positions and orientations of both bones can be tracked throughout the course of an operation to provide feedback to surgeons implanting a prosthetic device.

In another aspect, a computer implemented method for aligning a cutting guide for a total knee arthroplasty in a patient using a processing unit comprising a computer processor coupled to a non-transitory memory, a receiver, and a display is provided. The method can include receiving by the processing unit orientation data wirelessly from a first bone sensor attached to the patient's first bone, and receiving by the processing unit orientation data wirelessly from a first bone guide sensor, where the first bone guide sensor is attached to a first bone guide that includes probes for interfacing with the first bone in a known geometry. The method can further include calculating by the processing unit, based on the orientation data from the first bone guide sensor and the first bone sensor, angular offsets that calibrate the first bone sensor's orientation data to reflect the orientation of the mechanical axis of the first bone. The method can also include receiving by the processing unit orientation data wirelessly from a first bone cutting guide sensor that is attached to a first bone cutting guide that is connected to the patient, and displaying by the processing unit to a user a difference between the orientation of the mechanical axis of the first bone and the orientation of the first bone cutting guide.

As with the system described above, the computer implemented method can include any of a variety of additional or alternative steps or features. For example, in some embodiments the first bone can be a tibia, while in other embodiments the first bone can be a femur. In still other embodiments, the first bone cutting guide can be arranged to guide a cut that is oriented at a 90 degree angle to the mechanical axis of the first bone, though other angular orientations can also be employed.

In certain embodiments, the method can further include receiving by the processing unit orientation data wirelessly from a second bone sensor attached to the patient's second bone, and receiving by the processing unit orientation data wirelessly from a second bone guide sensor, where the second bone guide sensor is attached to a second bone guide that includes probes for interfacing with the second bone in a known geometry. The method can also include calculating by the processing unit, based on the orientation data from the second bone guide sensor and the second bone sensor, angular offsets that calibrate the second bone sensor's orientation data to reflect the orientation of the mechanical axis of the second bone. Still further, the method can include receiving by the processing unit orientation data wirelessly from a second bone cutting guide sensor that is attached to a second bone cutting guide that is connected to the patient, and displaying by the processing unit to a user a difference between the orientation of the mechanical axis of the second bone and the orientation of the second bone cutting guide.

In such embodiments, the first bone can be a tibia and the second bone can be a femur. Accordingly, the method can provide a surgeon with valuable feedback regarding the orientations of each bone.

In still another aspect, a method for aligning a cutting guide for total knee arthroplasty on a patient is provided that includes attaching a first bone sensor to the patient's first bone, where the first bone sensor can include a sensor for determining the orientation of the first bone sensor and a transmitter for transmitting orientation data wirelessly. The method can also include contacting a first bone guide to the patient's first bone, where the first bone guide has a plurality of probes configured to contact anatomical features of the first bone to establish a known geometry with respect to a mechanical axis of the first bone, and where the first bone guide includes a first bone guide sensor having a sensor determining the orientation of the first bone. The method can further include comparing the orientation data from the first bone guide sensor to the orientation data from the first bone sensor to calibrate the first bone sensor with respect to a mechanical axis of the first bone. The method can also include applying a first bone cutting guide to the patient's first bone, where the first bone cutting guide has one or more features for attaching to the patient's anatomy proximate to the first bone, and where the first bone cutting guide includes a first bone cutting guide sensor having a sensor determining the orientation of the first bone cutting. The method can further include comparing the orientation data from the first bone sensor with the orientation data from the first bone cutting guide sensor to determine the alignment between the first bone cutting guide and the mechanical axis of the patient's first bone.

As with the embodiments described above, the first bone can be a tibia in certain embodiments, and can be a femur in other embodiments. Further, in certain embodiments the cutting guide can be arranged to guide a cut that is oriented at a 90 degree angle to the mechanical axis of the first bone.

In some embodiments, the method can further include attaching a second bone sensor to the patient's second bone, where the second bone sensor has a sensor for determining the orientation of the second bone sensor and a transmitter for transmitting orientation data wirelessly. The method can also include contacting a second bone guide to the patient's second bone, where the second bone guide has a plurality of probes configured to contact anatomical features of the second bone to establish a known geometry with respect to a mechanical axis of the second bone, and where the second bone guide includes a second bone guide sensor having a sensor determining the orientation of the second bone guide. The method can further include comparing the orientation data from the second bone guide sensor to the orientation data from the second bone sensor to calibrate the second bone sensor with respect to a mechanical axis of the second bone. The method can also include applying a second bone cutting guide to the patient's second bone, where the second bone cutting guide has one or more features for attaching to the patient's anatomy proximate to the second bone, and where the second bone cutting guide includes a second bone cutting guide sensor having a sensor determining the orientation of the second bone cutting guide. Still further, the method can include comparing the orientation data from the second bone sensor with the orientation data from the second bone cutting guide sensor to determine the alignment between the second bone cutting guide and the mechanical axis of the patient's second bone.

In such embodiments, the first bone can be a tibia and the second bone can be a femur. Accordingly, the method can provide a surgeon with valuable feedback regarding the orientations of each bone. In addition, any of the various features or embodiments described above can be combined in any of a variety of manners, even if not stated explicitly here.

DETAILED DESCRIPTION OF THE INVENTION

Figure 1:
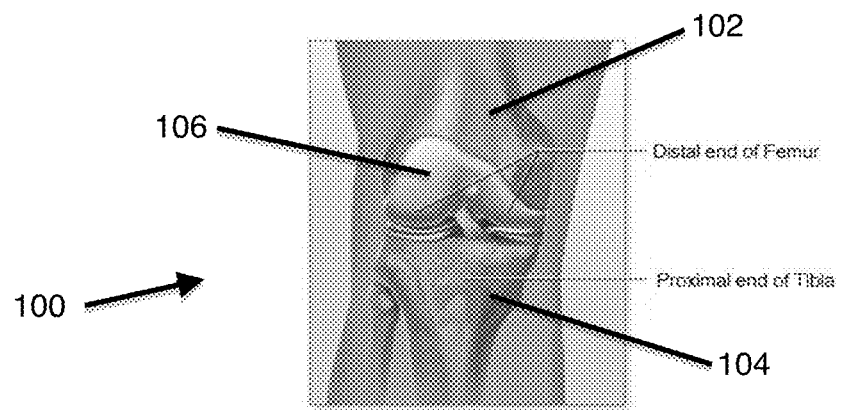
FIG. 1 illustrates the normal anatomy of a right knee.
Figure 2:
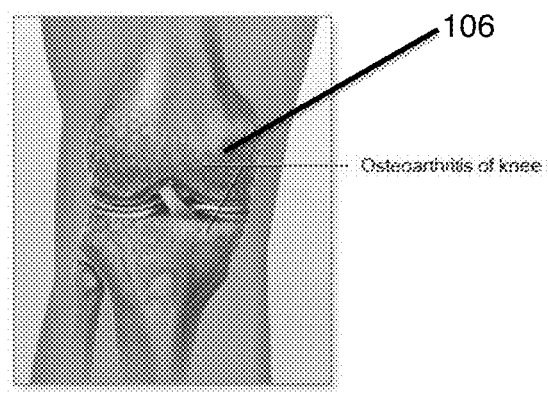
FIG. 2 illustrates an osteoarthritic right knee.
Figures 3A, 3B:
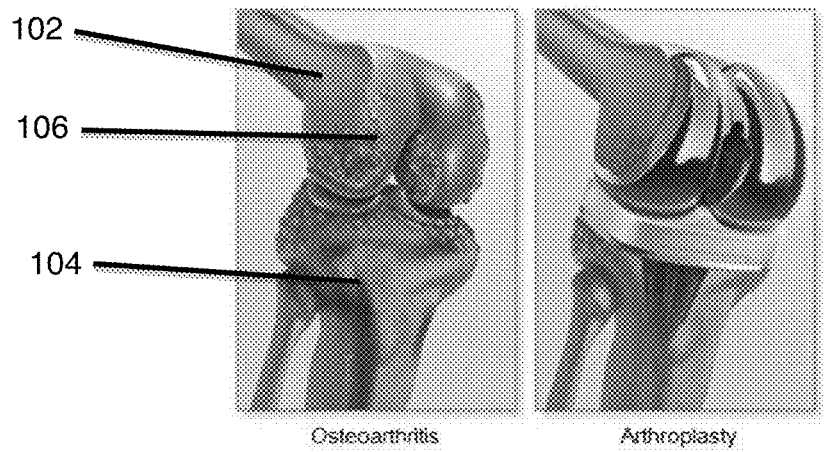
FIG. 3A illustrates another osteoarthritic right knee.
FIG. 3B illustrates a total knee arthroplasty.
Figure 4:
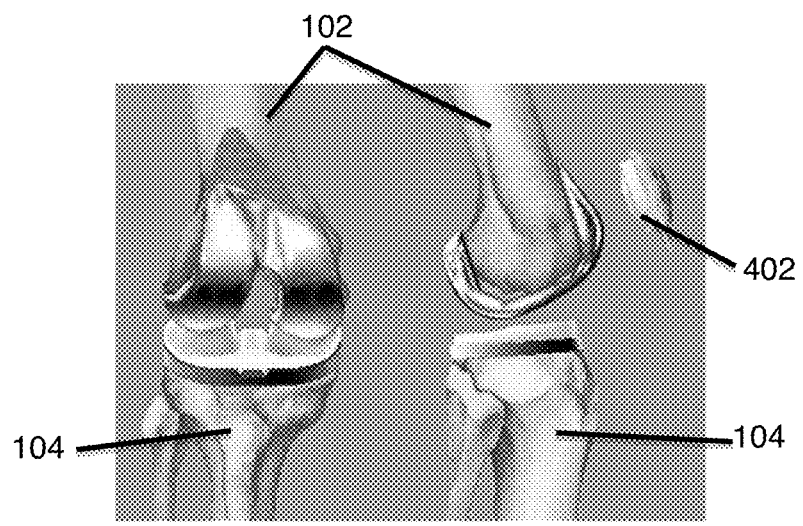
FIG. 4 illustrates prosthetic components implanted during knee arthroplasty.
Figure 5:
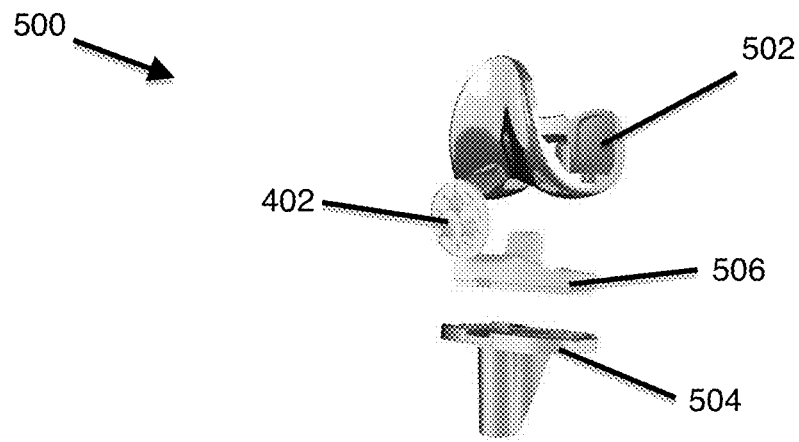
FIG. 5 illustrates an alternative view of prosthetic components implanted during knee arthroplasty.

The instant invention includes a novel apparatus, as well as a unique methodology and system, to measure, calculate, and monitor alignment of the long bones of the human lower limb for precise intra-operative bone preparation and positioning of prostheses, particularly with respect to avoiding misalignment of the reconstructed knee joint.

The systems described herein generally include a plurality of measuring sensor units that can detect their position and orientation in three-dimensional space and communicate this information to a digital data processor, e.g., via a wireless communication protocol. The measuring sensor units described herein can utilize inexpensive, highly accurate, digital components that are able to communicate with software running on a computer processor, personal computer (PC), or hand-held electronic device (e.g., a smartphone or electronic tablet), to accurately determine three-dimensional positioning of the femur and the tibia, as well as the angular position of cutting blocks or instruments. The positioning of these components can be monitored throughout the preparation of the bones to ensure that the reconstructed knee joint is properly aligned once the procedure is completed.

The determination of these positions and angles can be seen and read by a surgeon via a visual display, such as a portable digital display, thereby removing the need for a PC in certain embodiments. In some embodiments, the measuring system can continuously monitor the position of a patient's lower limbs and, as a consequence, the surgeon can effectively ensure an accurate angular placement of the cutting instruments in order to prepare the patient's native bone and restore the appropriate alignment of the leg. This can result in optimum functionality of the reconstructed joint and increase the patient's satisfaction following surgery.

The position sensing and monitoring systems described herein can be fast and easy to use, as well as accurate and precise in its determinations. Furthermore, it can be cost-efficient to operate. For example, the systems described herein require neither sophisticated equipment nor elaborate machinery, and are able to directly display the cutting guide instrument's placement, thereby avoiding any misalignment and eliminating the need for subsequent revision procedures to achieve stability in the reconstructed knee joint. In short, the devices, systems, and methods described herein can provide a precise and reliable tool for proper placement of prosthetic components during knee arthroplasty.

Words, Terms, and Titles

Although many of the words, terms, and titles employed herein are commonly employed and conventionally understood in their traditional medical usage and surgical context, a summary of detailed descriptive information and definitions is presented below for some human anatomic sites, for specific medical phrases and surgical applications, and for particular jargon, designations, epithets, or appellations. These points of information, descriptions, and definitions are provided herein to avoid the misinformation, misunderstandings, and ambiguities which often exist; as an aid and guide to recognizing the particulars of the present invention; and for appreciating the true scope and breadth of the present invention.

Figure 15:
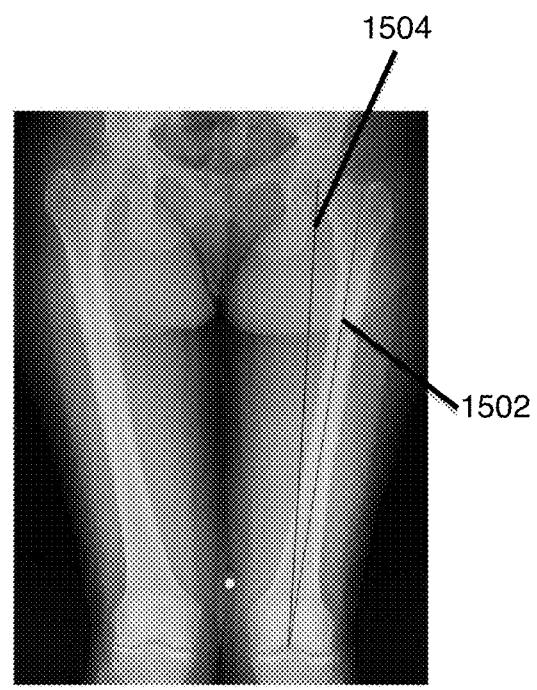
FIG. 15 illustrates anatomic and mechanical axes of a femur as determined in the templating step described below.

Anatomical Axis of the Femur: a straight imaginary line passing through the middle and along the shaft of the femur. An example anatomical axis of the femur 1502 is shown in FIG. 15.

Mechanical Axis of the Femur: a straight imaginary line that connects the center of rotation of the hip joint to the center of the knee. An example mechanical axis of the femur 1504 is shown in FIG. 15.

Figure 16:
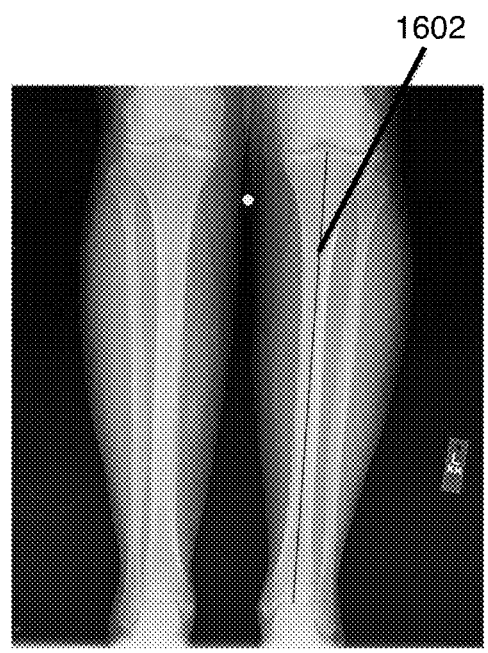
FIG. 16 illustrates an anatomic axis of the tibia (which is the same as a mechanical axis of the tibia) as determined in the templating step described below.

Anatomical Axis of the Tibia: an imaginary line passing through the middle and along the shaft of the tibia. An example anatomical axis of the tibia 1602 is shown in FIG. 16.

Mechanical Axis of the Tibia: the same line as the anatomical axis of the tibia.

Alignment: the relation between the mechanical axis of the femur and the tibia.

Figure 6:
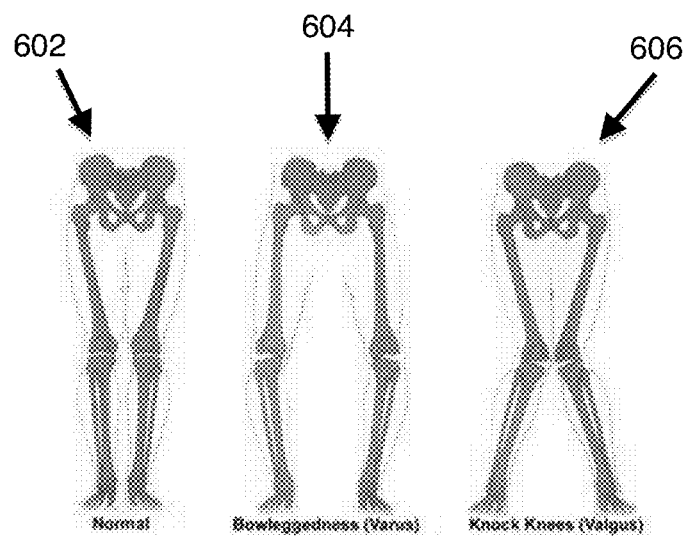
FIG. 6 illustrates (from left to right) normal, varus, and valgus knee alignments.
Figures 7A, 7B, 7C:
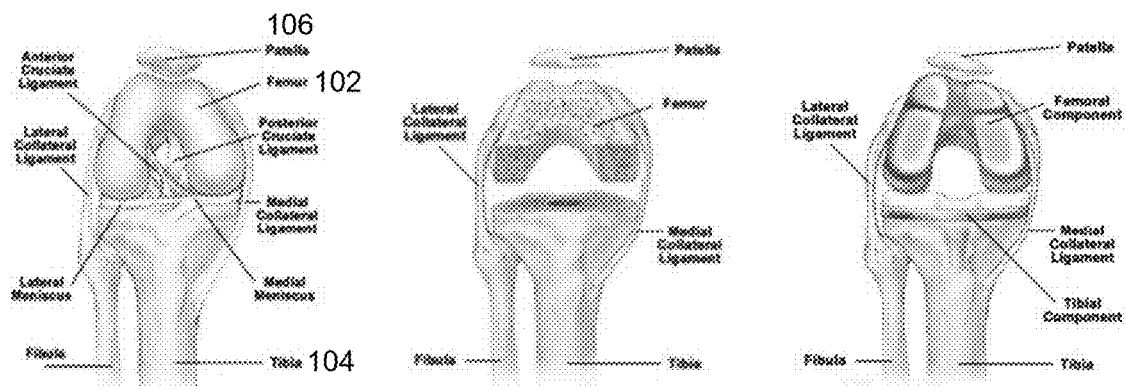
FIG. 7A illustrates one embodiment of pre-operative anatomy of a right knee.
FIG. 7B illustrates bone cuts to the knee of FIG. 7A required during knee arthroplasty.
FIG. 7C illustrates one embodiment of post-operative anatomy of the knee of FIG. 7A.
Figure 8:
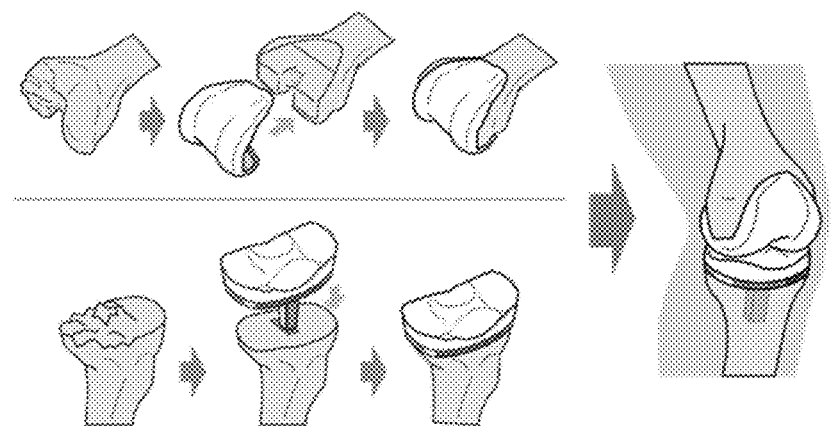
FIG. 8 illustrates one embodiment of a simplified procedure for knee arthroplasty.

Varus Deformity: when the intersection of the mechanical axis of the tibia and that of the femur falls outside the knee joint, resulting in a bowlegged deformity. An example of a varus deformity 604 is shown in FIG. 6.

Valgus Deformity: when the intersection of the mechanical axis of the tibia and that of the femur falls inside the knee joint, resulting in a knock-kneed appearance. An example of a valgus deformity 606 is shown in FIG. 6.

Slope: the angle between the cut surface of the tibia or the tibial component and the axis of the tibia in the coronal plane.

Anteroposterior (AP) View: an x-ray view taken from the front of the body to the back.

Lateral View: an x-ray taken from one side of the body.

System of the Invention/Components

The invention is primarily adapted for use in knee arthroplasty operations. It includes a novel system and a unique methodology to measure, calculate, and monitor position angles and alignment of elements of a patient's leg for precise intra-operative placement of femoral and tibial prostheses, particularly with respect to avoiding misalignment of the reconstructed joint.

Figure 11:
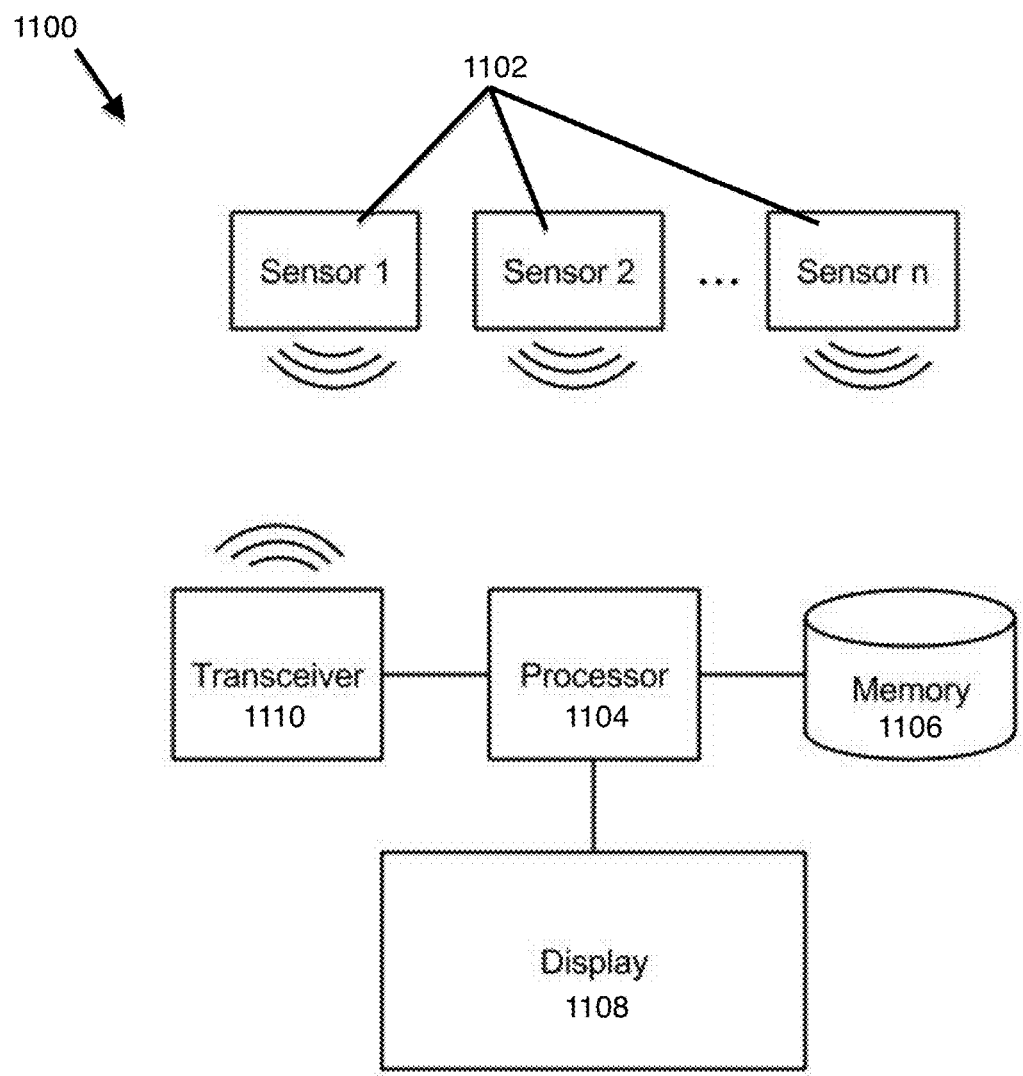
FIG. 11 illustrates components utilized in one embodiment of a system according to the teachings of the present invention.

FIG. 11 illustrates the basic components of one embodiment of a system according to the teachings of the present invention. The system 1100 can include one or more sensors 1102 that include a sensor capable of detecting the three-dimensional position and orientation of the sensor 1102 in space, as well as a transceiver or other communication component capable of transmitting position and/or orientation information to another component in the system. As explained in more detail below, the sensors 1102 can be coupled to various bones in the patient's body, as well as a variety of surgical guides, cutting blocks, or other instruments. The system 1100 can also include a digital data processor 1104 coupled to a non-transitory digital data store 1106, a display 1108, and a wireless transceiver 1110 or other communications component. The non-transitory digital data store 1106 can be any kind of computer-readable media, with the exception of a transitory, propagating signal. As explained below, the processor can receive information from the sensors 1102 via the transceiver 1110, and can execute application software stored in the data store 1106 to calculate any of a variety of information regarding the position of the patient's bones and alignment of the reconstructed joint. Results can be displayed to a surgeon or other user via the display 1108, which can be any of a variety of digital displays or other user interfaces known in the art.

More specifically, one embodiment of a system according to the teachings of the present invention can include one or more of the following enumerated elements:

1. A digital templating software, for evaluating the axes of long bones of the lower limb, i.e., the femur and the tibia, and measuring alignment and angles of flexion and/or extension of the knee joint.

2. An electronic tibia position sensor (TS), capable of sensing its orientation in 3-dimensional space and transmitting the information to the computer processor 1104. The TS can be attached to the shaft of the tibia and can transmit the position angles of the tibia to the computer processor 1104 and application software (see items 6 and 7 below). The position sensors 1102 used herein (including the TS and others described below) can each have at least one orientation sensor and at least one transmitter. The transmitter can be any of a variety of types used to transmit information, e.g., wirelessly, to a computer or tablet. In one embodiment, the sensors can include a BLUETOOTH transceiver. The orientation sensors can specify the tilt of the sensor with respect to orthogonal axes (such as x-y-z axes) and heading with respect to an external field (e.g., a natural or man-made magnetic field, etc.). In exemplary embodiments, accelerometers can be used to determine tilt and a magnetometer can be used to specify orientation with respect to natural or man-made magnetic fields.

Figure 17:
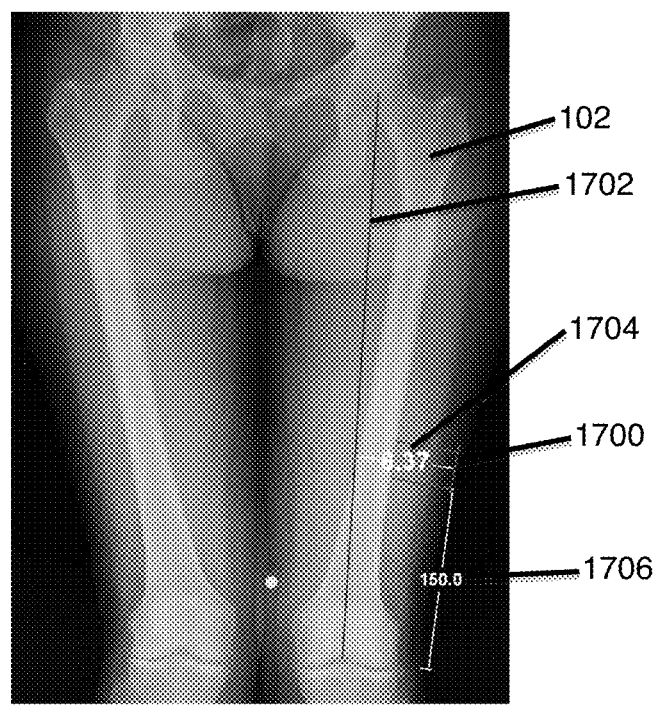
FIG. 17 illustrates step 1(*a*) of the templating portion of a procedure according to the teachings of the present invention.

3. An electronic femur position sensor (FS), capable of sensing its orientation in 3-dimensional space and transmitting the information to the computer processor. The FS can be attached to the shaft of the femur and can transmit the position angles of the femur to the computer processor 1104 and application software (see items 6 and 7 below). The FS sensor can be constructed similarly to the TS described above, and one embodiment of an exemplary FS 1700 is shown in FIG. 17.

Figure 13:
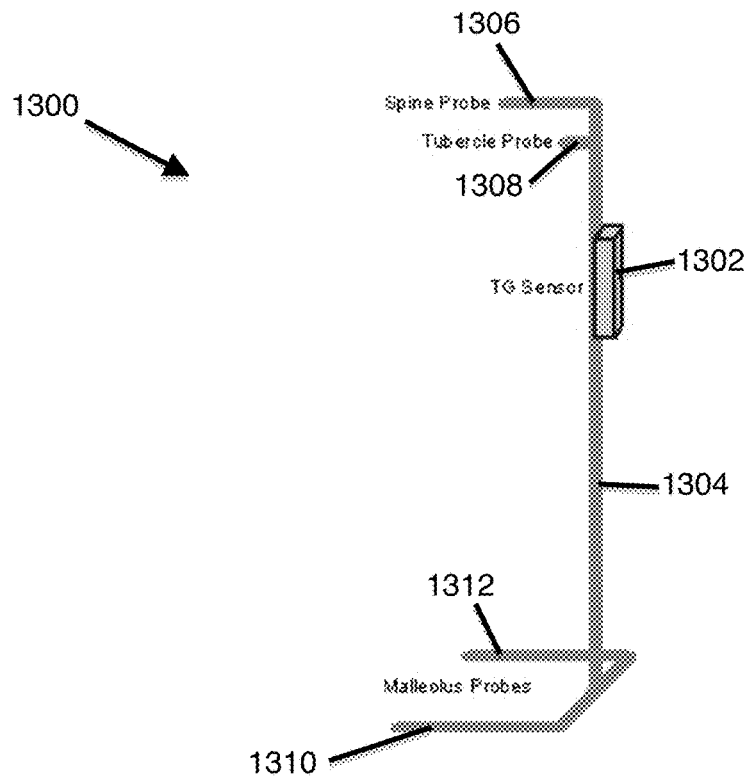
FIG. 13 illustrates one embodiment of a tibia guide.

4. A tibia axis guide (TG), an instrument used to reproduce the anatomic axis of the tibia. An exemplary tibia axis guide 1300 is shown in FIG. 13. The TG 1300 can include a metal frame with an attached electronic position sensor 1302 capable of sensing its orientation in 3-dimensional space and transmitting the information to the computer processor and application software (see items 6 and 7 below). The TG 1300 can in some embodiment include a vertical element 1304 on which the sensor 1302 is positioned. A superior (i.e., upper) end of the vertical element 1304 can include a spine probe 1306 and a tibial tubercle probe 1308. An inferior (i.e., lower) end of the vertical element can include two malleolus probes 1310, 1312. As will be explained below, the various probes on the TG 1300 can be used to locate the relevant anatomical features on the spine to establish the mechanical axis of the patient's tibia.

Figure 12:
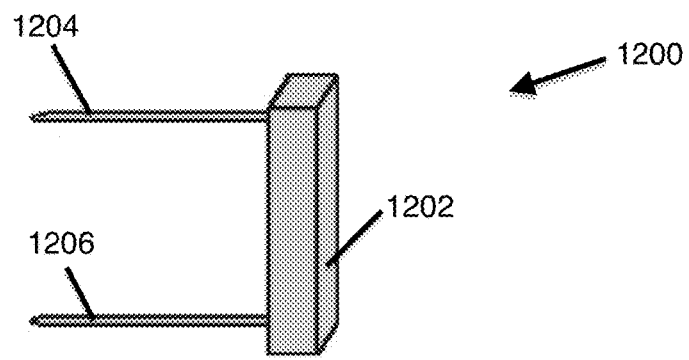
FIG. 12 illustrates one embodiment of a femur guide.

5. A femur axis guide (FG), for reproducing the anatomic axis of the femur. An exemplary femur axis guide 1200 is shown in FIG. 12. The FG 1200 can include an embedded electronic position sensor capable of sensing its orientation in 3-dimensional space and transmitting the information to the computer processor and application software (see items 6 and 7 below). The FG 1200 can also include a sensor 1202 (extending vertically in FIG. 12) with two probes 1204, 1206. The two probes 1204, 1206 (extending horizontally in FIG. 12) can be parallel and have the same length. As explained below, the probes 1204, 1206 can be used to contact the shaft of the femur to establish its orientation in at least one plane.

6. A computer processor (e.g., processor 1104), capable of running the application software (see item 7 below) and receiving the transmitted data from the various position sensors (e.g., the TS, FS, TG and FG). The computer processor can be a server, desktop, laptop, tablet, smart phone or any other stationary or mobile computer device having a processor coupled to a transceiver (e.g., transceiver 1110) that can communicate with the sensors described above, a memory (e.g., data store 1106) that can store sensor data and contain software instructions that will cause the processor to execute the functions disclosed herein, and a display (e.g., display 1108) for providing results to a user.

7. Application software, capable of (i) receiving the information transmitted by the TS, FS, TG and FG; (ii) calculating the various angles and/or positions of differing surgical tools and patient anatomy as described below, and (iii) displaying the position angles and calculating the angular relationships that aid a surgeon in placing the various guides and cutting blocks used in total knee arthroplasty. The application software can run on the computer processor described above.

Figure 14:
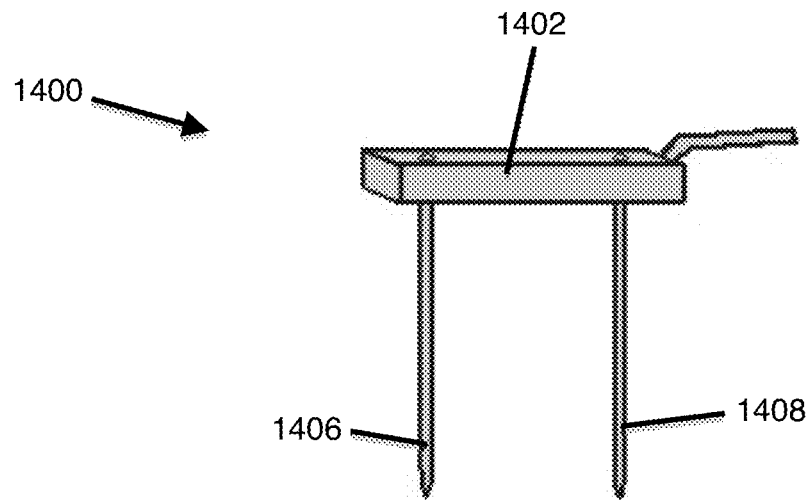
FIG. 14 illustrates one embodiment of a pin guide.

8. A pin guide for placing pins on the patient's anatomy to which one of the above-described sensors can be attached. An exemplary pin guide 1400 is illustrated in FIG. 14. The pin guide 1400 can have a horizontal base 1402 with two parallel and equal length cannulas 1406, 1408 extending away from the base. The cannulas 1406, 1408 can be arranged so that they can be used to contact a patient's bone to allow two pins to be inserted, one through each cannula, such that a sensor can be attached to the bone via the pins. For example, the probes 1204, 1206 can be extended through the cannulas 1406, 1408 to contact the femur.

9. Sets of metal pins, as known in the art.

Methods of the Invention

For ease of understanding and gaining a better appreciation of the subject matter of the present invention as a whole, a representative example describing parts of a knee joint replacement procedure is presented in detail below. It will be expressly understood, however, that the particular preferences and optimal details of this specific example are neither restrictive nor limiting of the method and system as a whole, and that many variations of the exemplary method and system are envisioned which may be advantageously and beneficially employed.

The methodology and system of the present invention can reveal angular position of the patient's lower limb long bones throughout the course of an operation. These position angles can, in turn, be used as reference points to determine the appropriate angular orientation of instruments used for surgical preparation of the patient's native bone, and consequently for placing a prosthesis in the best possible biomechanical position.

The methodology for precise intra-operative preparation of a patient's native bone and placement and positioning of a prosthesis as a surgical implant can be performed in accordance with the following steps:

Step 1: Templating

Figure 18:
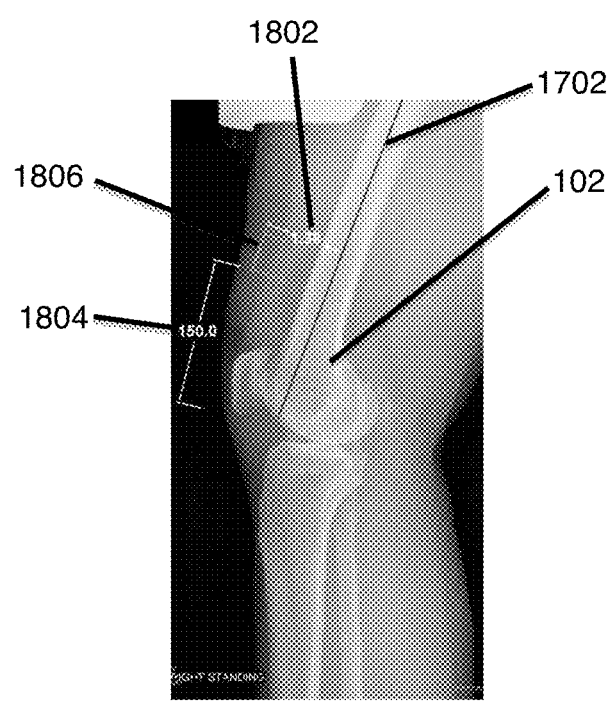
FIG. 18 illustrates step 1(*b*) of the templating portion of a procedure according to the teachings of the present invention.
Figure 19:
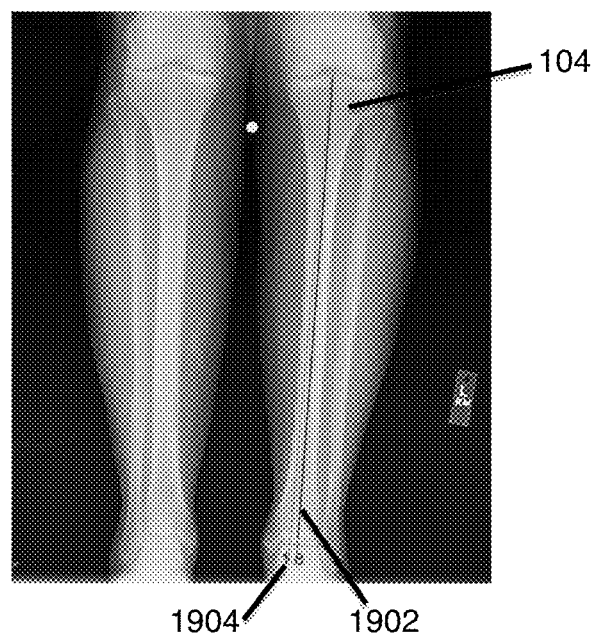
FIG. 19 illustrates step 1(*c*) of the templating portion of a procedure according to the teachings of the present invention.
Figure 20:
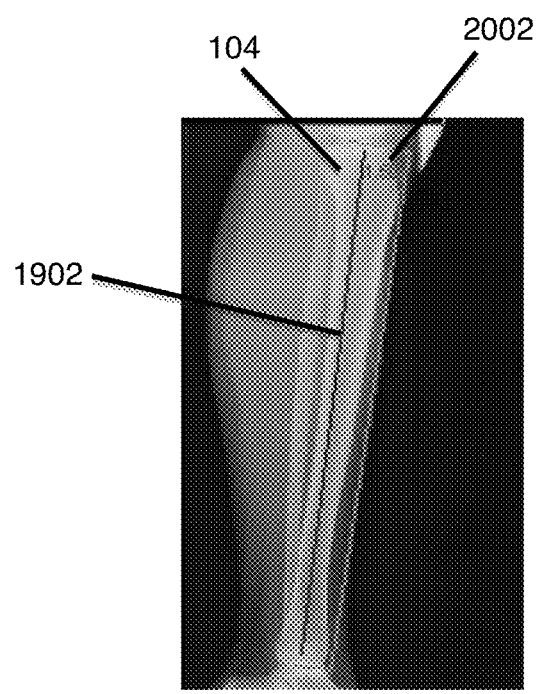
FIG. 20 illustrates step 1(*d*) of the templating portion of a procedure according to the teachings of the present invention.
Figure 21:
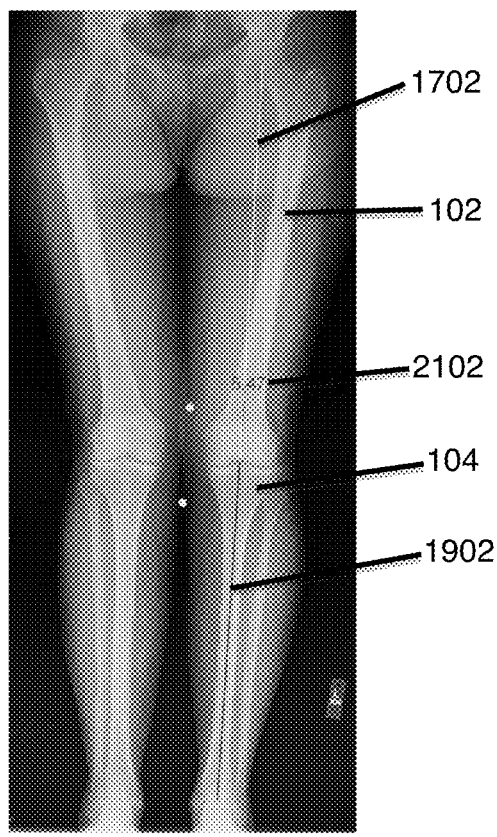
FIG. 21 illustrates step 1(*e*) of the templating portion of a procedure according to the teachings of the present invention.
Figure 22:
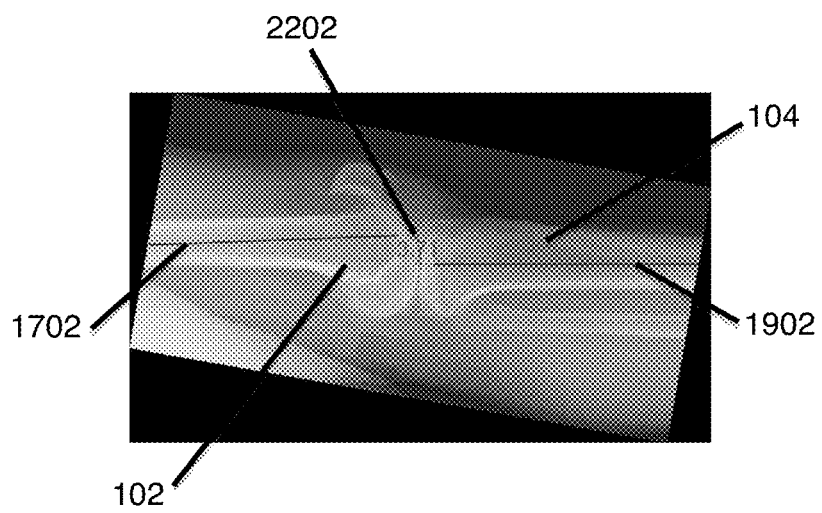
FIG. 22 illustrates step 1(*f*) of the templating portion of a procedure according to the teachings of the present invention.

Templating can include determining different axes and alignments by evaluating routine preoperative anteroposterior (AP) and lateral X-ray images. These can include the following elements:

a) A mechanical axis of the femur, a position angle of the FS or FG in relation to the mechanical axis (e.g., in an AP view), and a distance of the FS or FG from the joint line. FIG. 17 illustrates one example of an FS 1700 coupled to a femur 102, and shows a mechanical axis of the femur 1702, a position angle 1704 of the FS 1700 relative thereto, and a distance 1706 of the FS from the joint line.

b) A mechanical axis of the femur and a position angle of the FS or FG in relation to this axis in a lateral view. FIG. 18 illustrates one example of an FG coupled to a femur 102 at location 1806, and shows the mechanical axis of the femur 1702, a position angle 1802 of the FS or FG relative thereto, and a distance 1804 of the FS or FG from the joint line.

c) An axis of the tibia and a position angle of the TG in relation to this axis in an AP view. FIG. 19 illustrates one example of an axis of the tibia 1902 and a position angle 1904 of a TG (not shown) relative thereto.

d) An axis of the tibia and a position angle of the TG in relation to this axis in a lateral view. FIG. 20 illustrates one example of the axis of the tibia 1902 and a position angle 2002 of a TG (not shown) relative thereto.

e) A rest position alignment (RPA) of the knee, in AP view. FIG. 21 illustrates one example of an RPA, as shown by an alignment offset angle 2102 of the mechanical axis of the femur 1702 and the axis of the tibia 1902.

f) A rest flexion angle (RFA) of the knee, in lateral view. FIG. 22 illustrates one exampled of an RFA, as shown by an alignment offset angle 2202 of the mechanical axis of the femur 1702 and the axis of the tibia 1902.

The templating step can be completed using image-viewing software routinely employed by surgeons. Such software can include ArthroPlan, a digital templating software that includes tools and templates for this purpose and is available from ArthroCAD, Inc., of Ayer, Mass.

The templating step can be performed at any time and in any place. In some embodiments, it can be completed before starting an operation. The remaining steps described below can be done during the procedure in an operating room, e.g., after induction of anesthesia, as well as after prepping and draping a patient's lower limb in a fashion known in the art.

Step 2: Placement of the Femur Sensor (FS)

First, the pin guide 1400 can be used to place two pins in a patient's femur that can be used to secure the femur sensor (FS) relative thereto. The two cannulas 1406, 1408 of the pin guide 1400 can be passed through two incisions (e.g., 3 mm incisions in some embodiments) made by a surgical knife into the skin over a predetermined location along the shaft of the femur, until a tip of both cannulas 1406, 1408 comes into contact with the bone. Two attachment pins (not shown) can then be passed through the cannulas 1406, 1408 and driven into the femoral shaft. The tips of both cannulas 1406, 1408 should remain in contact with the bone when the pins are being placed in the femur. The pin guide 1400 can then be removed. The FS can then be coupled to the pins in a manner known in the art, thereby yielding a device that can look similar to the FG 1200 shown in FIG. 12.

In one embodiment, the predetermined location can be as illustrated in FIG. 17. More particularly, FIGS. 17 and 18 illustrate the possible placement of two sensors: the femur sensor (FS) 1700 and the femur guide (FG) 1200 that has a sensor disposed thereon. In FIG. 17 that shows an AP view, the FS 1700 is placed laterally on the femur 102. In FIG. 17, the vertical line shown at 1700 corresponds to the sensor and the horizontal lines shown at 1700 correspond to the pins on which the sensor is mounted. In this embodiment, the sensor is mounted 150.0 mm superiorly to the joint line between the femur and the tibia, as shown by distance 1706. While spacing other than 150.0 mm can be used (such as 200.0 mm, for example), the goal is to place the sensor so that it represents the straight lateral edge of the femoral shaft. Because this edge can be estimated as having a 6.37 degree angular difference from the mechanical axis of the femur 1702, the orientation of the mechanical axis 1702 in the visible plane can be estimated with a high degree of accuracy.

The FS 1700 can alternatively be placed in the position 1806 shown in FIG. 18, which provides a side or lateral view. If placed here, the sensor (represented by the vertical line at 1806) is positioned anteriorly to the femur 102. The pins (represented by the horizontal lines at 1806) can be placed using the pin guide 1400 in a similar fashion as in the preceding paragraph. In this position, the edge of the bone, and thus the sensor, would extend along an axis having a difference of 1.38 degrees in angulation from the mechanical axis of the femur 1702 in the illustrated plane, and the orientation of the mechanical axis 1702 can be estimated from the sensor data.

Once the pins have been placed in the desired position, the FS 1700 can be attached to the pins and secured. As is explained in step 6 below, the FG 1200 can be positioned orthogonally to the FS 1700. Accordingly, if the FS 1700 is placed as shown in FIG. 17, the FG can be placed as shown in FIG. 18, and vice versa. The FG 1200 can be used to calibrate the orientation of the FS 1700 such that, after a successful calibration, the FG 1200 can be removed and the orientation of the mechanical axis of the femur 1702 in both the AP and lateral planes can be determined using the sensor data from the FS 1700 alone.

Step 3: Placement of the Tibia Sensor (TS)

The pin guide 1400 can be used for placing two attachment pins in the shaft of the tibia at a predetermined location, following the same procedure as in Step 2 above. The pins can be placed in a similar fashion to the pins placed in the femur, including using the spacing of 150.0 to 200.0 mm inferiorly from the joint line.

Once the pins have been placed in the desired position, the TS can be attached to the pins and secured, thereby yielding a device that can be similar to the FG 1200 shown in FIG. 12.

Step 4: Establishing Connection and Starting Communication

Figure 23:
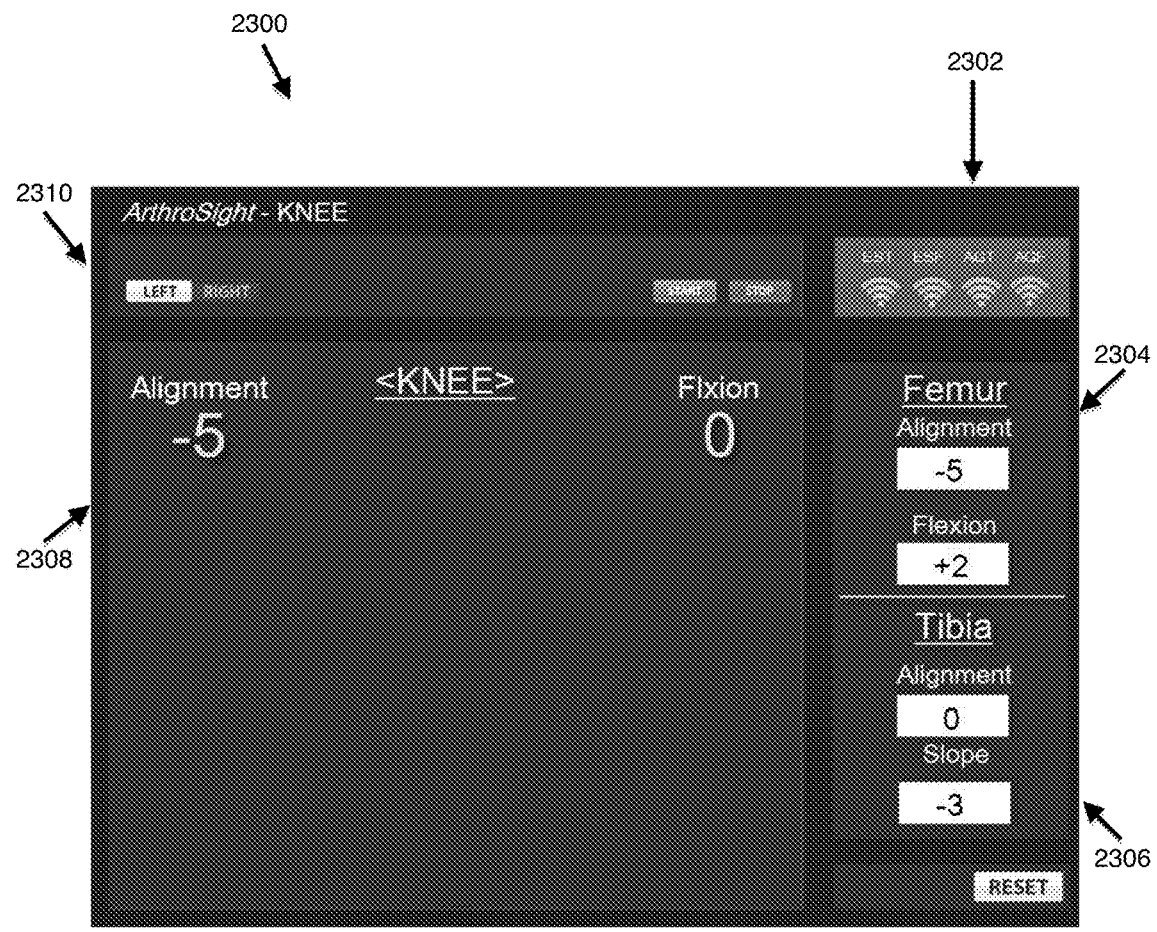
FIG. 23 illustrates one embodiment of a display window of application software according to the teachings of the invention.

Both the FS and the TS can be turned on and communication can be established with the application software running on the processor unit. This can be confirmed using the application software by changing the position of the patient's leg and confirming that the changing orientation of the sensors is being tracked by the processor. FIG. 23 illustrates one embodiment of a user interface 2300 that can be displayed to a user (e.g., via the display 1108). As shown in the figure, the interface 2300 can show connection status and strength 2302 to the various sensors in use, data 2304 related to the position of the femur, data 2306 related to the position of the tibia, and data 2308 related to the alignment and/or position of the knee joint. Further, this data can be toggled between left and right legs of the patient using switch 2310 in a case where a double knee arthroplasty is being performed. Accordingly, a surgeon can confirm connection and communication with the various sensors in use by checking the interface (e.g., portion 2302 in particular) and by moving the patient's leg and observing values shown on the display to confirm that they update.

Step 5: Reproducing the Anatomic Axis of the Tibia

After initial incision and exposure of the tibia, the tibia guide (TG) 1300 can be placed in contact with the tibial tubercle and the medial malleolus bony landmarks of the tibia in a flexion position. The position angles of the TG 1300 can be read by the application software while the leg is held in a stable position. These numbers can be used by the software to calibrate the orientation readings from the TS as the true anatomic and mechanical axes of the tibia. That is, the sensor 1302 on the tibia guide 1300 can provide a true orientation of the axis of the tibia 1902. This orientation can be compared to the orientation of the tibia sensor (TS) and offsets for the measured angles can be stored. These offsets can then be added back to the TS readings to determine the orientation of the axis of the tibia at any time, even as the patient's lower leg is moved and after the TG 1300 has been removed.

Step 6: Reproducing the Anatomic Axis of the Femur

The two pointing probes 1204, 1206 of the FG 1200 can be passed through the skin over the anterior side of the femur 102 at a location determined in Step 1 above until both come into contact with the femoral shaft. The FG 1200 can be held against and along the femur in a stable position for a short while until software reads the position angle. In the illustrated embodiment, the FG 1200 can be placed orthogonally to the FS (e.g., the FG 1200 can be positioned at location 1806 shown in FIG. 18 when the FS 1700 is placed as shown in FIG. 17). The application software can then use the FG position angle number and templated angle number to calculate the true position angle of the femur in the plane of the FG 1200 and the mechanical axis 1702 of the femur 102. This data can be used to calibrate the FS 1700 for this plane. The FS 1700 can then be used to determine the orientation of the mechanical axis of the femur 1702 in both the AP and lateral views shown in FIGS. 17 and 18. Once such a calibration is complete, the FG 1200 can be removed or, in other embodiments, can be left in place for the remainder of the operation.

In another embodiment, the original position of the pins can be used as the reference point if determined to be close to an anatomic axis when templating.

In another embodiment, the rest flexion angle (RFA) can be used for calibrating the position angle of the femur readings from the FS 1700.

Step 7: Navigating the Tibial Cut

Figure 10:
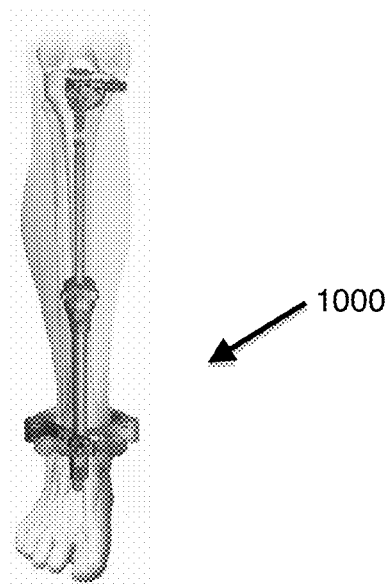
FIG. 10 illustrates one embodiment of an extra-medullary alignment device used for cutting the proximal tibia.

The electronic sensor unit 1302 can be detached from the TG 1300 and attached to a mechanical external tibial alignment device, such as the device 1000 shown in FIG. 10 that is used by surgeons for positioning a tibial cutting block. The application software can show the real time position angles of the cutting block (because it now has a sensor on its alignment device 1000) and the calibrated tibial axis information transmitted by the TS (which is similar to the FS 1700 and can be attached to the tibia 104 in a similar manner), and can alert the surgeon to misalignment. The cutting block can be fixed in a desired position in a fashion known in the art, and also fixed in a desired alignment with the tibial axis. A tibial cut can then be made.

Step 8: Navigating the Femoral Cut

Figure 9:
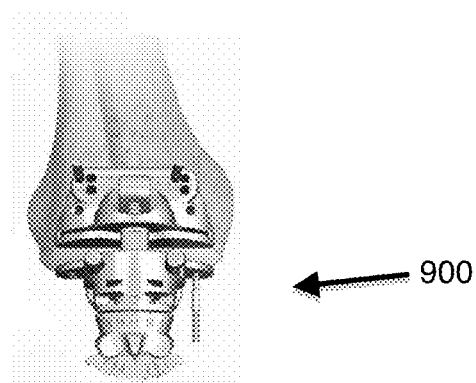
FIG. 9 illustrates one embodiment of an intra-medullary alignment device used for cutting the distal femur.

The electronic sensor unit 1202 can be detached from the FG 1200 and attached to a mechanical external femoral alignment device, such as the device 900 shown in FIG. 9 that is used by surgeons for positioning a femoral distal cutting block. The application software can show the real time position angles of the cutting block (because it now has a sensor placed on its alignment device 1000) and the real time position angles of the mechanical axis of the femur 1702 based on calibrated data transmitted by the FS 1700. The application software can further alert a surgeon to any misalignment between the cutting block and the mechanical axis of the femur 1702. The cutting block can be fixed in a desired position in a fashion known in the art, and also fixed in a desired alignment with respect to the mechanical axis of the femur 1702. A femoral distal cut can then be made.

The application software can be used to continuously monitor the real time position angles by receiving data from the electronic position sensors and calculating the relative angles. The information can be visually displayed on a computer's screen, or otherwise presented or conveyed to a user. FIG. 23 illustrates one embodiment of an interface 2300 that can be displayed to a user and can include position angles and alignment data for the femur, tibia, and knee joint.

Aside from the steps detailed above, known TKA surgical techniques can be followed during the remainder of the operation. The FS, TS, and pins can be removed at the end of operation.

Advantages and Benefits of the Invention

The present invention provides a surgeon with many advantages and desirable benefits over prior art TKA alignment techniques. Among them can be the following:

Precision: The electronic position sensors can be very precise and sensitive. When the procedure is done properly, the position angles can be highly accurate. Mechanical devices, on the other hand, can have accuracy limitations that result from being positioned visually and without a precise calibration.

Ease of Use: The apparatus of the present invention can be set up and used by any member of a surgical team after a short period of training. This is in marked contrast to computerized navigation systems that require a long period of technical training before being used and have a longer learning curve.

Reliability: Taking advantage of precise and accurate components, devices and systems according to the teachings of the present invention can provide reliable information to aid in proper alignment.

Simplicity: The present invention employs only a few small basic components and can use any conventional computer processor, PC, or hand-held electronic device. This fact makes the apparatus far less vulnerable to malfunction and failures; and allows for easier replacement of component parts if and when necessary. In comparison, computerized navigation requires one or two large camera units and a highly sophisticated computer, and it uses many different probes for registration.

Compact Size: The apparatus of the present invention, apart from the axis guide and the PC in certain embodiments, is very small in size and light in weight. In practice, the apparatus does not take up any meaningful space in the operating room and does not need a large inventory space. In addition, there is no equipment to be maintained outside of the operating room.

In comparison, computerized navigation systems can be bulky and heavy. They can only be used in large operating rooms. In addition to their large size, since the system has to be kept out of the sterile operating field while the cameras aim at the special spheres with no object passing in between them, the true setup requires even more space and limits the number of the assistants or trainees that can be present. Further, the equipment has to be kept in a storage area when are not being used.

Low Cost of Acquisition: The true cost of the present invention is estimated to be low, a small fraction of a computerized navigation system.

Time Savings: By helping surgeons to optimally prepare the patient's native bone during an initial TKA procedure, there is no need to reevaluate and/or recut bones. As a result, the present invention can considerably shorten the time needed for completing the operation.

Cost Savings: By shortening the operation time, the present invention also lowers the expense of the surgical operation and increases the productivity of surgeons and operating rooms.

Reduced Morbidity: By properly positioning prosthetic implants at the correct anatomical angles, the present invention can increase the durability of the prosthesis and lower any risk for revision operations in future. In addition, by shortening the operation time, the risk of infection is also lowered.

Increase Patients' Satisfaction: It is obvious that better anatomical alignment will result in better function and higher patient satisfaction.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A computer implemented method for aligning a cutting guide for a total knee arthroplasty in a patient using a processing unit comprising a computer processor coupled to a non-transitory memory, a receiver, and a display, the method comprising:
   i) receiving by the processing unit orientation data wirelessly from a first bone sensor attached to the patient's first bone;
   ii) receiving by the processing unit orientation data wirelessly from a first bone guide sensor, the first bone guide sensor being attached to a first bone guide that includes probes for interfacing with the first bone in a known geometry;
   iii) calculating by the processing unit, based on the orientation data from the first bone guide sensor and the first bone sensor, angular offsets that calibrate the first bone sensor's orientation data to reflect the orientation of the mechanical axis of the first bone;
   iv) receiving by the processing unit orientation data wirelessly from a first bone cutting guide sensor that is attached to a first bone cutting guide that is connected to the patient;
   v) displaying by the processing unit to a user a difference between the orientation of the mechanical axis of the first bone and the orientation of the first bone cutting guide;
   vi) receiving by the processing unit orientation data wirelessly from a second bone sensor attached to the patient's second bone;
   vii) receiving by the processing unit orientation data wirelessly from a second bone guide sensor, the second bone guide sensor being attached to a second bone guide that includes probes for interfacing with the second bone in a known geometry;
   viii) calculating by the processing unit, based on the orientation data from the second bone guide sensor and the second bone sensor, angular offsets that calibrate the second bone sensor's orientation data to reflect the orientation of the mechanical axis of the second bone;
   ix) receiving by the processing unit orientation data wirelessly from a second bone cutting guide sensor that is attached to a second bone cutting guide that is connected to the patient; and
   x) displaying by the processing unit to a user a difference between the orientation of the mechanical axis of the second bone and the orientation of the second bone cutting guide.

2. The method of claim 1, wherein the first bone is a tibia.

3. The method of claim 2, wherein the first bone cutting guide is arranged to guide a cut that is oriented at a 90 degree angle to the mechanical axis of the first bone.

4. The method of claim 1, wherein the first bone is a femur.

5. The method of claim 1, wherein the first bone is a tibia and the second bone is a femur.

6. A computer implemented method for aligning a cutting guide for a total knee arthroplasty in a patient using a processing unit comprising a computer processor coupled to a non-transitory memory, a receiver, and a display, the method comprising:
   i) receiving by the processing unit orientation data wirelessly from a tibia sensor attached to the patient's tibia;
   ii) receiving by the processing unit orientation data wirelessly from a tibia guide sensor, the tibia guide sensor being attached to a tibia guide that includes probes for interfacing with the tibia in a known geometry;

iii) calculating by the processing unit, based on the orientation data from the tibia guide sensor and the tibia sensor, angular offsets that calibrate the tibia sensor's orientation data to reflect the orientation of the mechanical axis of the tibia;

iv) receiving by the processing unit orientation data wirelessly from a tibia cutting guide sensor that is attached to a tibia cutting guide that is connected to the patient;

v) displaying by the processing unit to a user a difference between the orientation of the mechanical axis of the tibia and the orientation of the tibia cutting guide;

vi) receiving by the processing unit orientation data wirelessly from a femur sensor attached to the patient's femur;

vii) receiving by the processing unit orientation data wirelessly from a femur guide sensor, the femur guide sensor being attached to a femur guide that includes probes for interfacing with the femur in a known geometry;

viii) calculating by the processing unit, based on the orientation data from the femur guide sensor and the femur sensor, angular offsets that calibrate the femur sensor's orientation data to reflect the orientation of the mechanical axis of the femur;

ix) receiving by the processing unit orientation data wirelessly from a femur cutting guide sensor that is attached to a femur cutting guide that is connected to the patient; and x) displaying by the processing unit to a user a difference between the orientation of the mechanical axis of the femur and the orientation of the femur cutting guide.

7. The method of claim 6, wherein the tibia cutting guide is arranged to guide a cut that is oriented at a 90 degree angle to the mechanical axis of the tibia.

\* \* \* \* \*